United States Patent [19]

Papenfuhs et al.

[11] Patent Number: 5,087,725

[45] Date of Patent: Feb. 11, 1992

[54] PROCESS FOR THE PREPARATION OF ALKYL NITROBENZOATES

[75] Inventors: Theodor Papenfuhs, Frankfurt am Main; Reiner Hess, Weisbaden; Andreas Fuss, Karlstein, all of Fed. Rep. of Germany

[73] Assignee: Hoechst Aktiengesellschaft, Frankfurt am Main, Fed. Rep. of Germany

[21] Appl. No.: 513,661

[22] Filed: Apr. 24, 1990

[30] Foreign Application Priority Data

Apr. 26, 1989 [DE] Fed. Rep. of Germany ....... 3913781

[51] Int. Cl.$^5$ ............................................ C07C 205/00
[52] U.S. Cl. ..................................................... 560/20
[58] Field of Search ........................................... 560/20

[56] References Cited

U.S. PATENT DOCUMENTS 3,322,772  5/1967  Togashi et al. .................... 560/21

*Primary Examiner*—Jose G. Dees
*Assistant Examiner*—Porfirio Nazario
*Attorney, Agent, or Firm*—Connolly & Hutz

[57] ABSTRACT

A process for the preparation of alkyl ($C_1$–$C_3$) nitrobenzoates by reacting the nitrobenzoic acid to be esterified with an excess of about 300 to about 600 mol % of an alkanol ($C_1$–$C_3$) in a solvent which is inert towards the starting compounds and the reaction product in the presence of a polyfluoroalkanesulfonic acid of the general formula (1)

$$Y(C_nF_{2n})SO_3H \qquad (1)$$

in which Y is a hydrogen or fluorine atom, with the proviso that, if Y is H, this hydrogen atom is in the β-position relative to the sulfo group, or the hydrate thereof as catalyst in an amount of about 0.1 to about 20 mol %, relative to the nitrobenzoic acid used, at temperatures from about 60° to about 120° C.

10 Claims, No Drawings

PROCESS FOR THE PREPARATION OF ALKYL NITROBENZOATES

The present invention relates to a simple and advantageous process, compared with the prior art, for the preparation of alkyl nitrobenzoates by esterification of nitrobenzoic acids with lower alkanols in the presence of polyfluoroalkanesulfonic acids or their hydrate as catalyst.

Alkyl nitrobenzoates are in general prepared analogously to the reaction scheme below

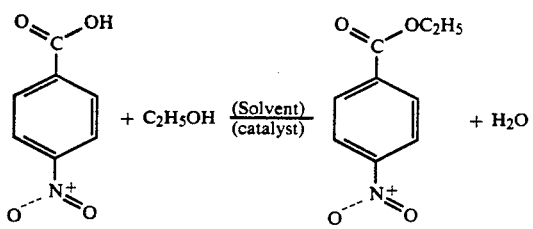

which shows the preparation of ethyl 4-nitrobenzoate, i.e. by treating nitrobenzoic acid with ethanol in the presence of sulfuric acid (B. 71 (1938), 335, 338 or J. Chin. Chem. Soc. 13 (1946), 22, 24 or M. 66 (1935) 316, 326). The purities and yields obtained in this reaction are moderate, since the reaction only comes into being due to the dehydrating effect of the sulfuric acid, which, however, simultaneously gives rise to various side reactions, such as sulfonation and oxidation, and is therefore unsuitable as "solvent" for the esterification.

Further possibilities of esterification consist in working with dialkyl sulfates as O-alkylating agents in the presence of basic catalysts, such as dicyclohexylamine (Stodola, J. Org. Chem. 29 (1964), No. 8, 2490-91), or with diazoalkanes (J. Labelled Compd. Radiopharm. 1983, 20 (9), 1047-59). However, due to the extreme toxicity of the alkylating agents used, both possibilities are only viable in combination with a very high degree of safety precautions on an industrial scale.

Furthermore, a large number of alkylating agents exists whose lack of commercial availability prevents their use on an industrial scale: alkyl phosphite/diethyl azodicarboxylate (Pol. J. Chem. 1982, 56 (1), 149-52), alkoxy- and alkylthiomethyleneiminium salts (Yukagaku 1984, 33 (11), 776-9), trialkyloxonium salts (J. Org. Chem. 44 (1979) 7, 1149).

An overview of the various alkylating agents on a laboratory scale is given in the volume "Carboxylic acid derivatives" (HOUBEN-WEYL, "Methoden der Organischen Chemie" (Methods of organic chemistry), Volume E 5, Part 1, pages 659 ff.), in which interalia tetraalkyloxysilanes and chlorosilanes and various derivatives of phosphoric acid are also mentioned as O-alkylating agents for carboxylic acids. The common features of all reagents listed there are the complicated preparation procedure, which in some cases can be carried out in the manner described only on a laboratory scale, and the significant toxicity of highly reactive alkylating agents (such as, for example, diazomethane). Accordingly, no application describing the use of the alkylating agents mentioned for the synthesis of nitrobenzoates is to be found.

The reaction of 4-nitrobenzoic acid with 1400 mol % of methanol at 190° C. in two process steps is described as an industrial preparation process for, for example, methyl 4-nitrobenzoate (DE 3,335,312-C): in this process, the acid is first heated with half the amount of alcohol under pressure, then cooled and let down, the water formed—together with the methanol—is then distilled off, methanol is again added, and the mixture is again heated to 190° C. under pressure. Despite the complexity of the apparatus (autoclave; number of steps), this process only gives a yield of 93% of theory, and especially the moderate space yield caused by the high methanol excess and the very moderate space-time yield due to the many process steps must be criticized.

In a different Laid-Open Application (SU 455,943), the preparation of ethyl 4-nitrobenzoate is described as follows: 4-nitrobenzoic acid is refluxed at 80° C. with 370 mol % of ethanol in the presence of 79 mol % of ammonium hydrogen sulfate—i.e. almost an equimolar amount. Work-up is carried out via a phase separation not described in more detail and crystallization from ethanol. The yield given in this process is 95.5% of theory. No mention is made of the possibility of recycling the bottom layer containing the catalyst added in an almost molar amount; nor is the grade of the final product characterized.

What has been said above concerning the reaction with sulfuric acid is true when working with ammonium hydrogen sulfate: the grade and appearance of the product are only moderate due to side reactions with sulfuric acid or hydrogen sulfate. To this is added the only slightly lower corrosivity of the hydrogen sulfate in dilute form compared with dilute sulfuric acid, which makes it necessary to work in corrosion-resistant materials (Hastelloy and the like).

There was therefore a demand for an industrial process for the preparation of nitrobenzoates of low alkanols (R—OH where R=CH$_3$, C$_2$H$_5$ or C$_3$H$_7$) which operates with a catalyst which is added in "truly" catalytic amounts and can be recycled without regenerating it if at all possible and does not give rise to side reactions with the starting compounds or the reaction product, as, for example, sulfuric acid does.

It has now been found that alkyl (C$_1$-C$_3$) nitrobenzoates can be prepared in a simple and advantageous manner by reacting nitrobenzoic acid with an excess of about 300 to about 600 mol %, preferably about 400 to about 500 mol % of an alkanol (C$_1$-C$_3$) in a solvent which is inert towards the starting compounds and the reaction product in the presence of a polyfluoroalkanesulfonic acid of the general formula (1)

$$Y(C_nF_{2n})SO_3H \qquad (1)$$

in which Y is a hydrogen or fluorine atom, with the proviso that, if Y is H, this hydrogen atom is in the β-position relative to the sulfo group, or the hydrate thereof as catalyst in an amount of about 0.1 to about 20 mol %, preferably about 2 to about 10 mol %, particularly advantageously about 2 to about 4 mol %, relative to the nitrobenzoic acid used, at temperatures from about 60° to about 120° C., preferably about 62° to about 108° C., particularly preferably from about 62° to about 95° C.

The catalyst of the formula (1) mentioned, which is used in the process according to the invention, for example the tetrafluoroethanesulfonic acid or the hexafluoropropanesulfonic acid or their monohydrates completely fulfils the conditions required, in that no side reactions caused by the catalyst occur in this process and the catalyst itself can be recovered by a simple aqueous extraction from the reaction solution formed and can be recycled into the following batch without any further regeneration.

2-Nitro-, 3-nitro- and 4-nitrobenzoic acid can be used as the nitrobenzoic acid to be esterified.

Examples of suitable inert solvents are benzene, toluene, xylenes, chlorobenzene, ethylbenzene, carbon tetrachloride, chloroform, cyclohexane, 1,2-dichloroethane, isopropyl ether, methyl butyl ether, methyl butyl ketone, methyl ethyl ketone or propyl isopropyl ether.

The detailed procedure of the process according to the invention is as follows: the nitrobenzoic acid to be esterified is initially introduced as a solution in the inert solvent, and the polyfluoroalkanesulfonic acid is added as such or in the form of the hydrate (catalyst) in an amount of about 0.1 to about 20 mol %, preferably about 2 to about 10 mol %, particularly advantageously about 2 to about 4 mol %, relative to the number of moles used of the nitrobenzoic acid. The solution is heated to about 60°–about 120° C., preferably about 62°–about 108° C. The addition of 300–600 mol %, preferably 400–500 mol % of alkanol (ROH where R is $CH_3$, $C_2H_5$ or $C_3H_7$) is then started and carried out in such a manner that the boiler temperature of the reaction mixture does not drop below about 60° C. and does not exceed about 105° C. At the same time, a mixture of the alkanol added, the inert solvent and the water formed in the reaction is continuously distilled off.

After the addition of the alkanol is completed and after an appropriate period of after reaction, the distillation temperature increases, thus indicating that the esterification is completed. This is followed by distilling off a mixture of the alkanol and the solvent, and the mixture is finally cooled down to room temperature by stirring.

The reaction (esterification) can be carried out at atmospheric, reduced or superatmospheric pressure.

The extraction of the catalyst to be used again in the following batches is carried out in 1–5, preferably 2–3, extraction steps each using 1–20% by volume, preferably 1.5–3% by volume, of water, relative to the volume of the reaction batch.

This is followed by a wash cycle using aqueous alkali to remove small traces of unconverted nitrobenzoic acid. The solvent is then distilled off, if necessary by means of steam and the nitrobenzoic ester is separated off as a melt (bottom layer).

In the examples which follow, individual nitrobenzoic esters are used to illustrate that the reaction can be carried out in a simple manner. It should be pointed out again that the catalyst extracts can be recycled into the following batch without any further work, and the water of the extraction is then distilled off during the reaction.

EXAMPLE 1

350 g (2.1 mol) of 3-nitrobenzoic acid, 700 g of toluene and 13.6 g of hexafluoropropanesulfonic acid hydrate (0.0544 mol=2.6 mol %, relative to 3-nitrobenzoic acid) are weighed into a 2-l four-necked flask equipped with stirrer, inside thermometer, dosage unit with inside temperature control and distillation head, and the mixture is heated to 95° C. with stirring. The temperature-controlled addition of 188 g (4.0 mol) of ethanol is then started, and immediately after starting the addition a ternary mixture consisting of ethanol, water and toluene distills off, which separates upon cooling into two layers, one of which contains mainly water and the other mainly ethanol. The addition of ethanol is controlled in such a manner that, depending on the inside temperature, the addition is stopped as soon as the temperature drops below 95° C., to avoid supersaturation of the reaction mixture in ethanol.

After 8 hours of addition, the reaction is completed, after which time a total of 92 g of ternary mixture has been distilled off (78 g of bottom layer and 14 g of top layer).

Subsequently 149 g of a binary mixture of ethanol and toluene are distilled off, during which bottom temperatures of up to 105° C. in a slight vacuum are maintained.

The mixture is then washed three times with 50 ml of water each to give a total of 148 g of washing liquor, which contains the hexafluoropropanesulfonic acid hydrate and is recycled directly into the subsequent batch.

Subsequently the mixture is washed three times with 100 ml of 5% sodium hydroxide solution each to remove unconverted nitrobenzoic acid. This gives 325 or 315 ml of washing liquor, from which the 3-nitrobenzoic acid is recovered by acidification and filtration with suction.

The toluene solution of the product is then poured into 1000 ml of water, and the solvent toluene is distilled off with steam. This gives 694 g of toluene, which can be recycled into the following batch.

The product is separated off as the bottom layer at 60° C. in a separator funnel to give 397 g of moist ethyl 3-nitrobenzoate, which is dried by incipient distillation at 100 mbar up to a temperature of 120° C. The yield obtained is 387 g of dry ethyl 3-nitrobenzoate, which corresponds to a yield of 94.7% of theory of melting point 39.7° C. and a purity of 98.6% by HPLC.

The procedure as described in the previous example is repeated, except that the same amount of benzene, xylene, chlorobenzene or ethylbenzene is used instead of the 700 g of toluene, to give in each case the same result.

EXAMPLE 2

350 g of 2-nitrobenzoic acid (2.1 mol), 700 g of toluene and 10 g of hexafluoropropanesulfonic acid hydrate are initially introduced into a 2-l four-necked flask equipped as described in Example 1, the mixture is heated to 95° C., and 188 g of ethanol (4.2 mol) are added using the procedure of Example 1.

Using the same work-up as in Example 1, this example gives 380 g of moist ethyl 2-nitrobenzoate and, after drying, 376 g of dry ethyl 2-nitrobenzoate, which corresponds to a yield of 92% of theory, of melting point 29.8° C. and a purity of 96.9% by HPLC.

EXAMPLE 3

700 g of toluene, 190 g of ethanol, 350 g of 4-nitrobenzoic acid and 7 g of tetrafluoroethanesulfonic acid hydrate are weighed into a 2-l four-necked flask equipped as described in Example 1. The procedure described in Example 1 is then repeated. Using the work-up described in Example 1 gives 368 g of ethyl 4-nitrobenzoate and, after drying, 361 g of dry ethyl 4-nitrobenzoate, which corresponds to a yield of 88.3% of theory, in a purity of 98.9% by HPLC.

EXAMPLE 4

700 g of toluene, 235 g of ethanol (5.2 mol), 350 g of 4-nitrobenzoic acid and 10 g of hexafluoropropanesulfonic acid hydrate are weighed into a 2-l four-necked flask equipped as described in Example 1. The procedure described in Example 1 is then repeated. Using the work-up described in Example 1 gives 386 g of ethyl 4-nitrobenzoate and, after drying, 382 g of dry ethyl 4-nitrobenzoate, which corresponds to a yield of 94.4% of theory, in a purity of 99.2% by HPLC of solidification point 56° C.

EXAMPLE 5

700 g of cyclohexane, 350 g of 4-nitrobenzoic acid (2.1 mol) and 10 g of hexafluoropropanesulfonic acid hydrate are initially introduced into a 2-l four-necked flask equipped as described in Example 1, the mixture is heated to 80° C., and the addition of 230 g (5.0 mol) of ethanol is started at this temperature. The subsequent procedure and the work-up are analogous to Example 1. This example gives 399 g of moist ethyl 4-nitrobenzoate and, after drying by incipient distillation, 383 g of dry ethyl 4-nitrobenzoate, which corresponds to 94.5% of theory, of melting point 55.8° C. in a purity of 98.2% by HPLC.

The procedure described in the previous example is repeated, using the same amount of carbon tetrachloride, chloroform, cyclohexane, 1,2-dichloroethane, isopropyl ether, methyl butyl ether, methyl butyl ketone, methyl ethyl ketone or propyl isopropyl ether instead of the 700 g of cyclohexane, to give in each case the same result.

We claim:

1. A process for the preparation of alkyl ($C_1$-$C_3$) nitrobenzoates, which comprises reacting the nitrobenzoic acid to be esterified with an excess of about 300 to about 600 mol % of an alkanol ($C_1$-$C_3$) in a mixture consisting essentially of a solvent which is inert towards the starting compounds and the reaction product and a polyfluoroalkanesulfonic acid of the general formula (1)

$$Y(C_nF_{2n})SO_3H \qquad (1)$$

in which Y is a hydrogen or fluorine atom, with the proviso that, if Y is H, this hydrogen atom is in the β-position relative to the sulfo group, or the hydrate thereof as catalyst in an amount of about 0.1 to about 20 mol %, relative to the nitrobenzoic acid used, at temperatures from about 60° to about 120° C.

2. The process as claimed in claim 1, wherein the reaction is carried out at temperatures from about 62° to about 108° C.

3. The process as claimed in claim 1, wherein the reaction is carried out in the presence of tetrafluoroethanesulfonic acid or hexafluoropropanesulfonic acid or their hydrates.

4. The process as claimed in claim 1, wherein the reaction is carried out with an excess of about 400 to about 500 mol % of alkanol ($C_1$-$C_3$).

5. The process as claimed in claim 1, wherein the reaction is carried out in the presence of about 2 to about 10 mol % of a polyfluoroalkanesulfonic acid of the general formula (1) mentioned in claim 1 or its hydrate.

6. The process as claimed in claim 1, wherein 2-nitro-, 3-nitro-, or 4-nitrobenzoic acid is reacted.

7. The process as claimed in claim 1, wherein the reaction is carried out in benzene, toluene, xylene, chlorobenzene, ethylbenzene, carbon tetrachloride, chloroform, cyclohexane, 1,2-dichloroethane, isopropyl ether, methyl butyl ether, methyl butyl ketone, methyl ethyl ketone or propyl isopropyl ether as the inert solvent.

8. The process as claimed in claim 1, wherein the reaction is carried out under reduced pressure.

9. The process as claimed in claim 1, wherein the reaction is carried out at superatmospheric pressure.

10. The process as claimed in claim 1, wherein the excess alkanol ($C_1$-$C_3$) is added to the initially introduced nitrobenzoic acid which is dissolved in the inert solvent, the solution of which also contains the catalyst, at temperatures from about 62° to about 108° C.

* * * * *